United States Patent [19]

Wilson et al.

[11] Patent Number: 4,781,861

[45] Date of Patent: Nov. 1, 1988

[54] AZIDE-TERMINATED AZIDO COMPOUND

[75] Inventors: Edgar R. Wilson, Simi Valley; Milton B. Frankel, Tarzana, both of Calif.

[73] Assignee: Rockwell International Corporation, El Segundo, Calif.

[21] Appl. No.: 134,537

[22] Filed: Dec. 15, 1987

Related U.S. Application Data

[63] Continuation of Ser. No. 56,026, Jun. 1, 1987, abandoned.

[51] Int. Cl.[4] ...................... C07C 77/02; C07C 117/00

[52] U.S. Cl. ...................................... 260/349; 558/484

[58] Field of Search .......................... 260/349; 558/484

[56] References Cited

U.S. PATENT DOCUMENTS

| | | | |
|---|---|---|---|
| 1,686,344 | 10/1928 | Rinkenbach | 558/484 |
| 1,751,438 | 3/1930 | Bergeim | 558/484 X |
| 1,936,020 | 11/1933 | Hough | 558/484 |
| 2,518,245 | 8/1950 | Morris et al. | 558/484 X |
| 2,853,511 | 9/1958 | Boedecker et al. | 558/484 X |
| 4,268,450 | 5/1981 | Frankel et al. | 260/349 |
| 4,440,687 | 4/1984 | Witucki et al. | 260/349 |
| 4,450,110 | 5/1984 | Simmons et al. | 260/349 |
| 4,486,351 | 12/1984 | Earl | 260/349 |

OTHER PUBLICATIONS

Wilson, et al.; *Journal of Chemical and Engineering Data,* (1982), 27, pp. 472–473.

*Primary Examiner*—Joseph Paul Brust

*Attorney, Agent, or Firm*—H. Fredrick Hamann; Harry B. Field; David C. Faulkner

[57] ABSTRACT

An energetic azide-terminated azido compound and a method for producing same is disclosed.

4 Claims, No Drawings

AZIDE-TERMINATED AZIDO COMPOUND

This is a continuation of co-pending application Ser. No. 056,026 filed on June 1, 1987, now abandoned.

BACKGROUND OF THE INVENTION

1. Field of the Invention

This invention relates to an energetic azide-terminated azido plasticizer, and is particularly directed to a method for producing this compound.

2. Description of Prior Art

Commercial polyalkalene ether glycols (1) have been nitrated to give the corresponding polyalkalene ether glycol dinitrates (2):

$$HO-(CH_2CH_2O)_nCH_2CH_2OH \xrightarrow{HNO_3}$$

1

$$O_2NO-(CH_2CH_2O)_nCH_2CH_2ONO_2$$

2 where n is an integer ranging from 1 to 10. Such nitrato compounds have proven to be useful energetic compositions, such as plasticizers, for propellants and explosives. An example is triethylene glycol dinitrate (n=2).

The conversion of such polyalkylene ether dinitrates to the corresponding diazides (3) has been reported in Wilson, E. R. and Frankel, M. B., *J. Chem. Eng. Data* 1982, 27, 472:

$$O_2NO-(CH_2CH_2O)_nCH_2CH_2ONO_2 \xrightarrow{NaN_3}$$

2

$$N_3-(CH_2CH_2O)_nCH_2CH_2N_3$$

3

Such compounds are also useful energetic plasticizers.

SUMMARY OF THE INVENTION

There is provided by the present invention a process for producing a glycidyl azide polymer azide having the general formula:

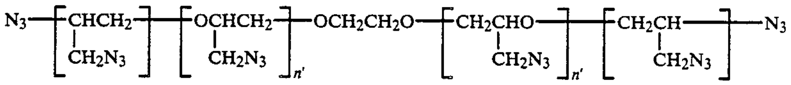

where n' is an integer from 0 to 9.

OBJECTS OF THE INVENTION

Therefore, it is an object of the present invention to provide improved materials useful in formulating solid propellants, explosives, and the like.

Another object of the present invention is to provide new compositions of matter.

An additional object of the present invention is to provide an energetic azide-terminated azido plasticizer.

Still another object of the present invention is to provide a new process for producing new compositions of matter.

DESCRIPTION OF THE PREFERRED EMBODIMENT

In accordance with the present invention there is provided a glycidyl azide polymer azide having the following structural formula:

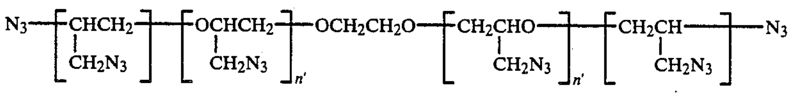

and a polyepichlorohydrin-nitrate having the following structural formula:

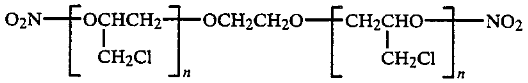

wherein n is an integer from 1 to 10.

By way of example and not limitation, the compounds of the present invention are prepared as follows:

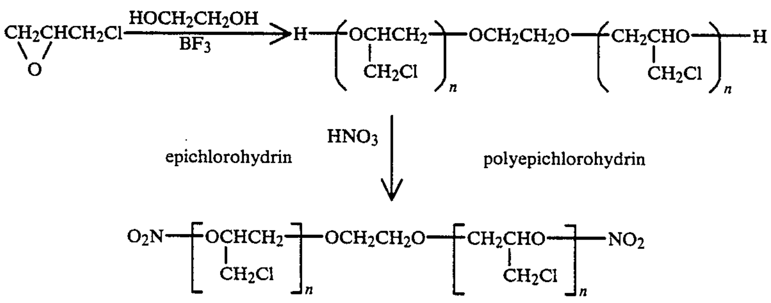

Polyepichlorohydrin-nitrate

-continued

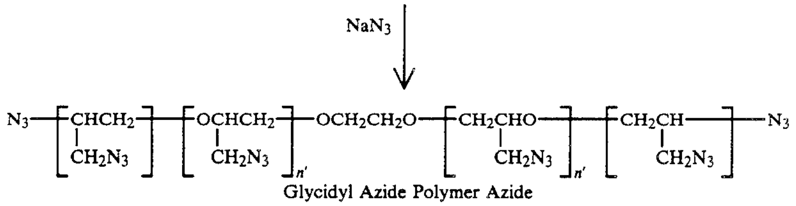

Glycidyl Azide Polymer Azide wherein n is an integer from about 1 to 10 n' is an integer from about 0 to 9.

In a suitable reaction vessel, a solution of 19.3 grams (0.3 moles) of 98% nitric acid, 20.4 grams (0.2 moles) of 96% sulfuric acid, and 51 milliters of methylene chloride was cooled to about 5° C. and a solution of 47.8 grams (0.1 moles) of polyepichlorohydrin (MW478) and 50 milliters of methylene chloride was added dropwise while maintaining the temperature at about 5° C. The polyepichlorohydrin was prepared by the polymerization of epichlorohydrin using an initiator such as ethylene glycol, propylene glycol or chloro-1,2-propanediol and a Lewis acid catalyst such as boron trifluoride.

This reaction mixture was stirred for an additional hour at about 5° C. and quenched on ice. The methylene chloride solution was separated, washed first with water and then with 5% sodium bicarbonate solution. The methylene chloride solution was then again washed with water and dried over anhydrous sodium sulfate and concentrated to provide 50.7 grams (89.3%) of polyepichlorohydrin-nitrate.

The polyepichlorohydrin-nitrate was next combined with 50 milliters of dimethylsulfoxide*, and 42.2 grams (0.65 moles) of sodium azide. This mixture was heated for about 8 hours at about 100° C., cooled, and quenched on water. The solution was extracted with 150 milliters of methylene chloride. The organic solution was next washed with 700 milliters of water 5 times and subsequently dried over anhydrous magnesium sulfate and then passed through a silica gel column. Concentration of the final solution gave 23.1 grams (43.8%) of glycidyl azide polymer azide. The product was characterized and identified as set forth in Table 1.

*NOTE: While dimethylsulfoxide is preferred, dimethylformamide may also be used as the organic solvent.

TABLE 1

NAME:
GLYCIDYL AZIDE POLYMER AZIDE

STRUCTURE:

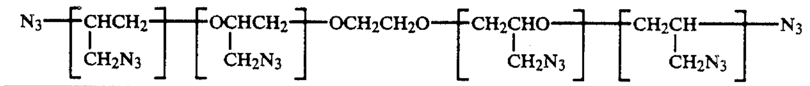

| | | | |
|---|---|---|---|
| FORMULA: | $C_{14}H_{24}N_{18}O_4$ | | |
| MOLECULAR WEIGHT: | 508 | | |
| ELEMENTAL ANALYSES: | C | H | N |
| Calculated: | 33.07 | 4.72 | 49.61 |
| Found: | 33.21 | 4.93 | 49.33 |
| INFRARED SPECTRUM: | $N_3$(4.7μ) | | |
| APPEARANCE: | Light Yellow Liquid | | |
| REFRACTIVE INDEX: | 1.5108 @ 28° C. | | |
| DENSITY: | 1.24 g/cc | | |
| FREEZING POINT: | −67° C. | | |
| DSC: | 187° C. (Onset of Exotherm) | | |
| WEIGHT LOSS: | 0.35% after 140 hrs at 74° C. | | |
| IMPACT SENSITIVITY: | 144 in-lb | | |
| $\Delta H_f$ | +273 Kcal/mole | | |

Obviously, numerous variations and modifications may be made without departing from the present invention. Accordingly, it should be clearly understood that the form of the present invention described above is illustrative only and is not intended to limit the scope of the present invention.

What is claimed and desired to be secured by Letters Patent of the United States is:

1. A glycidyl azide polymer azide of the general formula:

(1)

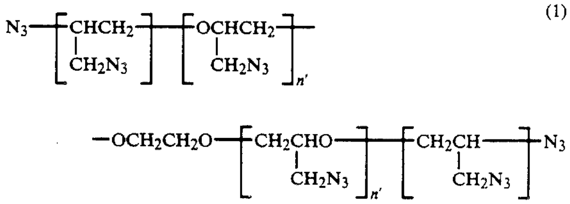

wherein n' is 0 to 9 and said glycidyl azide polymer azide is produced by the process of reacting polyepichlorohydrin-nitrate of the general formula:

(2)

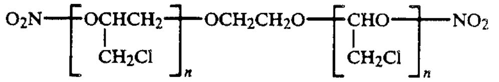

wherein n is 1 to 10, with sodium azide in a polar solvent.

2. Polyepichlorohydrin-nitrate of the general formula:

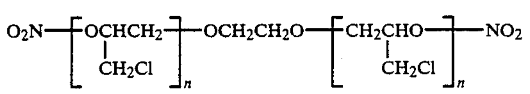

(1)

produced by the process by reacting polyepichlorohydrin of the general formula:

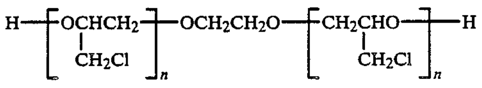

(2)

with $HNO_3$ and wherein n of formulas (1) and (2) is an integer from 1 to 10.

3. As a composition of matter, glycidyl azide polymer azide having the general formula:

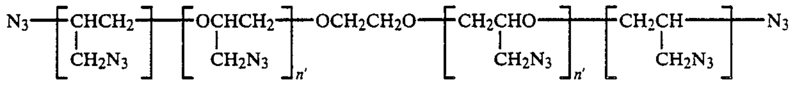

wherein n' is an integer from 0 to 9.

4. As a composition of matter, polyepichlorohydrinnitrate having the general formula:

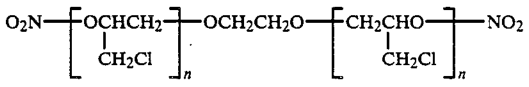

where n is an integer from 1 to 10.

* * * * *

UNITED STATES PATENT AND TRADEMARK OFFICE

CERTIFICATE OF CORRECTION

PATENT NO. : 4,781,861

DATED : Nov. 1, 1988

INVENTOR(S) : Edgar R. Wilson and Milton B. Frankel

It is certified that error appears in the above-identified patent and that said Letters Patent is hereby corrected as shown below:

Column 4, line 35, delete

" 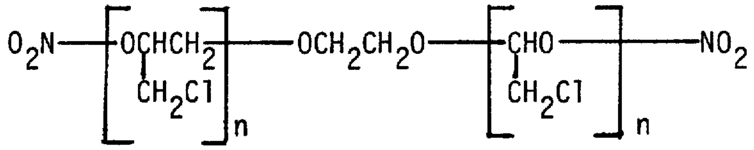 "

and insert --

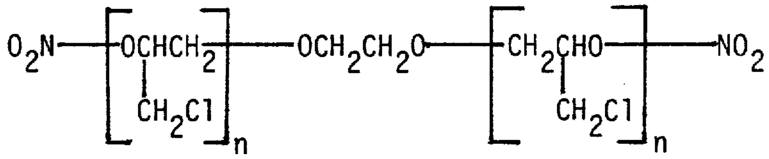 --

Signed and Sealed this

Seventh Day of March, 1989

*Attest:*

DONALD J. QUIGG

*Attesting Officer*

*Commissioner of Patents and Trademarks*